United States Patent [19]

Baggiolini et al.

[11] Patent Number: 4,632,784

[45] Date of Patent: Dec. 30, 1986

[54] PROCESS FOR THE PREPARATION OF 1α,23,25-TRIHYDROXYCHOLECAL-CIFEROL-26-OIC ACID 23,26-LACTONE

[75] Inventors: Enrico G. Baggiolini, North Caldwell; Milan R. Uskokovic, Upper Montclair; Peter M. Wovkulich, Nutley, all of N.J.

[73] Assignee: Hoffmann-La Roche Inc., Nutley, N.J.

[21] Appl. No.: 635,686

[22] Filed: Jul. 30, 1984

Related U.S. Application Data

[63] Continuation-in-part of Ser. No. 461,835, Jan. 23, 1983, abandoned.

[51] Int. Cl.[4] .................................................. C07J 3/00
[52] U.S. Cl. ................................... 260/397.2; 549/295
[58] Field of Search ..................... 260/239.57, 397.2

[56] References Cited

U.S. PATENT DOCUMENTS 4,307,231  12/1981  De Luca et al. ................. 260/397.2
4,336,193   6/1982  De Luca et al. ................ 260/239.57

FOREIGN PATENT DOCUMENTS 059881  4/1982  Japan .............................. 260/397.2

OTHER PUBLICATIONS

Proc. of the Fifth Workshop on Vitamin D, Feb. 1982-pp. 1089-1094 an article by Baggiolini et al.

*Primary Examiner*—Elbert L. Roberts
*Attorney, Agent, or Firm*—Jon S. Saxe; Bernard S. Leon; William G. Isgro

[57] ABSTRACT

The invention is directed to a process and intermediates for the preparation of 1α, 23,25-trihydroxycholecalciferol-26-oic acid 23,26-lactone.

6 Claims, No Drawings

PROCESS FOR THE PREPARATION OF 1α,23,25-TRIHYDROXYCHOLECALCIFEROL-26-OIC ACID 23,26-LACTONE

This application is a continuation-in-part of application Ser. No. 461,835, filed Jan. 23, 1983, now abandoned.

BRIEF SUMMARY OF THE INVENTION

The invention is directed to a process for the preparation of 1α,23,25-trihydroxycholecalciferol-26-oic acid 23,26-lactone of the formula

I which comprises the steps of (a) reacting a compound of the formula

II wherein $R^1$ is hydrogen, tri-lower alkylsilyl, aryl-di-lower alkylsilyl, diaryl-lower alkylsilyl or triarylsilyl, with a compound of the formula

III wherein $R^2$ is lower alkyl or aryl, to yield a compound of the formula

IV wherein $R^1$ and $R^2$ are previously described, and (b) removing the protecting groups from the product of step (a) whereby there is obtained the corresponding compound of formula I.

In another aspect the invention relates to intermediates of the formula

V wherein $R^3$ and $R^4$ each, independently, is hydrogen, tri-lower alkylsilyl, aryl-di-lower alkylsilyl, diaryl-lower alkylsilyl, triarylsilyl or a group of the formula $$-\underset{R^6}{\overset{R^5}{\text{C}}}-\text{O}-R^7$$

wherein $R^5$ is hydrogen or lower alkyl; and $R^6$ and $R^7$ each, independently, are lower alkyl or aryl and $R^6$ and $R^7$ taken together are lower alkylene of from 3 to 6 carbon atoms.

DETAILED DESCRIPTION OF THE INVENTION

As used throughout the specification and the appended claims, the term "lower alkyl" denotes a monovalent substituent consisting solely of carbon and hydrogen of from 1 to 8 carbon atoms which may be straight- or branched-chain. Examples of lower alkyl groups are methyl, ethyl, n-propyl, i-propyl, tert-butyl, hexyl, heptyl, octyl and the like. The term "lower alkylene" denotes a divalent substituent consisting solely of carbon and hydrogen of from 1 to 8 carbon atoms which may be straight- or branched-chain and whose free valences are attached to two distinct groups. Examples of alkylene groups are methylene, ethylene, propylene, butylene, amylene, hexylene, heptylene, octylene and the like. The term aryl denotes an organic radical derived from an aromatic hydrocarbon by the removal of a hydrogen atom. Exemplary of aryl are phenyl and substituted phenyl.

In the formulas represented herein the various substituents are illustrated as joined to the nucleus by one of the following notations: A solid line (━━) indicates that a substituent is in the β-orientation, (that is, above the plane of the molecule), a broken line (----) indicates that a substituent is in the α-orientation (that is, below the plane of the molecule), and a wavy line (∼∼∼) indicates that the substituent may be in either the β or α orientation or in a mixture of compounds containing substituents in the α and/or β orientation.

The invention comprises a process for the preparation of a compound of the formula

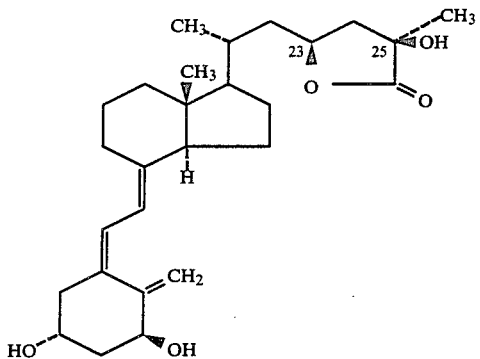
Ia its 23,25 diastereomers or mixtures thereof. The description which follows for the preparation of the compound of formula Ia is equally applicable for the preparation of each of the corresponding 23,25 diastereomers or mixtures thereof.

To prepare a compound of formula Ia by the process of the invention, a compound of the formula

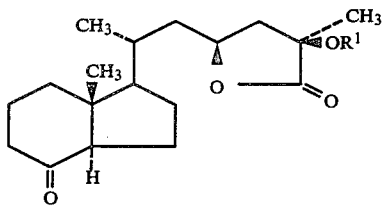
IIa wherein $R^1$ is hydrogen, tri-lower alkylsilyl, di-lower alkylarylsilyl, lower alkyl-diarylsilyl or triarylsilyl, is reacted with a compound of the formula

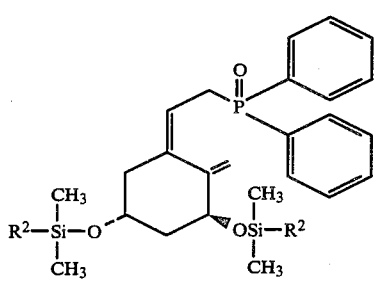
III wherein $R^2$ is lower alkyl or aryl, to yield a compound of the formula

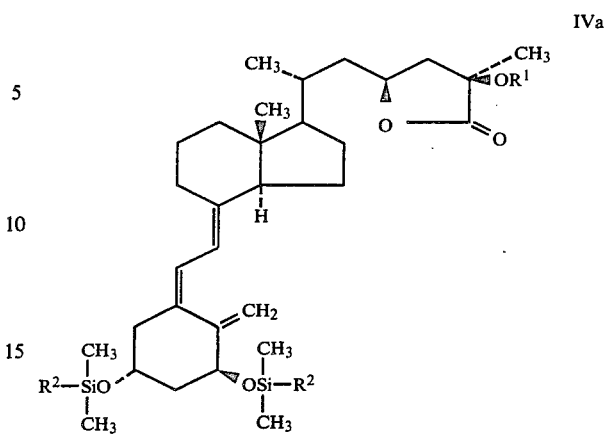
IVa wherein $R^1$ and $R^2$ are as previously described, and (b) removing the protecting groups from the compound of formula IVa, whereby there is obtained the compound of formula Ia.

It is understood that in place of a compound of formula IIa, there can be used one of the following diastereomers:

[3-S-[2 alpha,5R-5 alpha(R*),[1R*-(1 beta,3a alpha,7a beta)]]]-dihydro-5-[2-(octahydro-7a-methyl-1H-inden-4-one-1-yl)-2-methylethyl]-3-hydroxy-3-methyl-2(3H)-furanone,

[3R-[3 beta-5R-5 alpha(R*),(1R*),[1R*-(1 beta,3a alpha,7a beta)]]]-dihydro-5-[2-(octahydro-7a-methyl-1H-inden-4-one-1-yl)-2-methylethyl]-3-hydroxy-3-methyl-2(3H)-furanone, or

[3S-[3 alpha,5S-5 beta(R*),[1R*-(1 beta,3a alpha,7 a beta)]]]-dihydro-5-[2-(octahydro-7a-methyl-1H-inden-4-one-1-yl)-2-methylethyl]-3-hydroxy-3-methyl-2(3H)-furanone, or mixtures thereof, to obtain the corresponding diastereomeric 1α, 23,25-trihydroxycholecalciferol-26-oic acid 23,26-lactone or mixtures thereof.

In accordance with the invention, a ketone of the formula IIa is reacted with a phosphine oxide of the formula III, which are known compounds or can be prepared according to known procedures, to yield a compound of formula IV. The reaction is carried out in the presence of a base in a conventional ether solvent under an inert atmosphere at a temperature in the range of from about −80° C. to about −50° C. Exemplary of suitable bases are alkyl lithium compounds and alkali metal dialkylamides. The compound of formula IVa can be purified by elution chromatography on silica gel.

In the alternative a mixture of diastereomers of the formula II may be used as the starting material whereby the corresponding mixture of diastereomers of the formula IV is produced, which may be separated by elution chromatography on silica gel.

The compound of formula IVa is converted to the compound of formula Ia by removal of the hydroxyl derivatizing groups by treatment of the compound of formula IVa with alcohol or water in the presence of an acid. While any mineral acid or lower alkanoic or sulfonic acid may be used it is preferred to use a cationic ion exchange resin (for example, AG50W-X4, BioRad Laboratories, Amberlite CG120, Rohm and Haas Co. Amberlyst 15 Rohm and Haas Co., Dowex 50X4, Dow Chemical Co.) as a suspension in a lower alkyl alcohol. The product of the formula Ia is isolated by filtration of the solid cationic exchange resin and evaporation of the volatiles under reduced pressure.

The starting materials of the formula

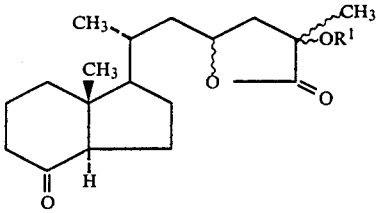 II can be prepared by the process hereinafter described. More particularly, an epoxide of the formula

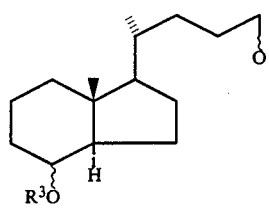 VI wherein $R^3$ is as previously described, is reacted with the compound of the formula

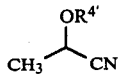 VII wherein $R^{4'}$ is as previously described but other than hydrogen, in the presence of a base in a conventional ether solvent, under an inert atmosphere, and at a temperature range of from about $-80°$ C. to $+70°$ C. to produce a mixture of compounds of the formula

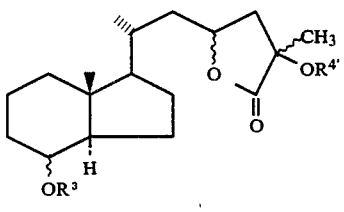 V wherein $R^3$ is as above and $R^{4'}$ is as previously described but other than hydrogen. If desired, the diastereomers thus produced may be separated by elution chromatography on silica gel. Exemplary of suitable bases are alkali and alkaline earth dialkyl or disilyl amides such as lithium diisopropylamide, potassium bis-trimethylsilylamide, bromomagnesium diisopropylamide or potassium hydride.

When $R^3$ and $R^4$ are other than hydrogen, the hydroxyl protecting groups are removed by treatment with a lower alkyl alcohol or water in the presence of an acid. The temperature is not critical. Suitable acids are mineral acids such as hydrochloric, sulfuric and the like, organic acids such as formic, trifluoro acetic, oxalic and the like, and sulfonic acids such as methanesulfonic, toluenesulfonic and the like.

The compound of formula V wherein $R^3$ and $R^4$ are hydrogen is converted to the compound of formula II wherein $R^1$ is hydrogen by treatment with an oxidizing agent. Suitable oxidizing agents are chromium based compounds among which are pyridinium chlorochromate, 2,3-dipyridinium chloromate, pyridine-chromium trioxide and the like, and activated dimethylsulfoxide. The synthetic application of activated dimethylsulfoxide has been reviewed extensively by A. J. Mancuso and D. Swern, Synthesis, 16S (1981).

The compound of formula II wherein $R^1$ is hydrogen may be converted to the compound of formula II wherein $R^{1'}$ is tri-lower alkylsilyl, aryl-di-lower alkylsilyl, diaryl-lower alkylsilyl or triarylsilyl by treatment with a silylating agent in the presence of a weak amine base. Typical silylating agents are trimethylchlorosilane, triethylchlorosilane, tertiary-butyldimethylchlorosilane and chlorodimethyl phenylsilane. Exemplary of suitable bases are imidazole, 4-dimethylaminopyridine, triazole and the like. A preferred silylating agent is trimethylsilyl imidazole which conveniently silylates the free hydroxyl group at room temperature.

The starting materials of formula VI can be prepared by the process hereinafter described. An ethylidene compound of the formula

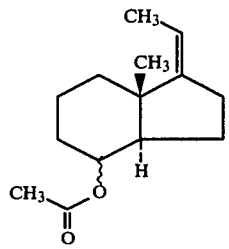 VIII is reacted utilizing an ene reaction with a lower alkyl-2-haloacrylate to yield, stereoselectively, with respect to the γ-position of the butanoic acid lower alkyl ester side chain, a compound of the formula

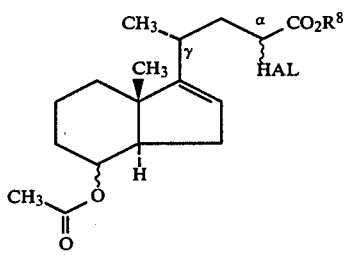 IX wherein $R^8$ is lower alkyl.

Generally it is preferred to carry out this reaction in the presence of a Lewis acid catalyst, in an inert solvent at temperatures in the range of from about 0° C. to room temperature. On the other hand elevated or reduced temperatures can be utilized.

Exemplary of conventional inert solvents are methylene chloride, carbon tetrachloride, chloroform, aromatic hydrocarbons such as benzene, toluene and the like, and lower aliphatic hydrocarbon solvents such as hexane, heptane, octane ahd the like. The reaction is carried out a temperatures in the range of from about $-20°$ to 100° C., the particular reaction temperature not being critical. The reaction is catalyzed by Lewis acid catalyst such as lower alkyl aliuminum dihalides and aluminum trihalides in weak base. Exemplary of such catalysts are ethylaluminum dichloride, aluminum tribromide in pyridine or aluminum chloride in pyridine, with ethylaluminum dichloride being particularly preferred.

If desired, the mixture of stereoisomers may be separated at this point by elution chromatography which will give about a 1:6 yield of the R to S stereoisomer at the α-position.

If desired, an equilibration procedure may be employed to produce a 1:1 mixture of R to S isomer starting from the R isomer, S isomer or mixtures thereof. The equilibration is carried out by reaction of a compound of the formula IX with lithium bromide. The temperature of this reaction is not critical. Generally it is preferred to carry out this reaction at room temperature in a polar solvent such as acetone, dimethylformamide, acetonitrile, dimethylsulfoxide, tetrahydrofuran and the like.

In the next step, the compound of formula IX is reduced by reaction with a hydride reducing agent in an inert organic solvent so as to yield a compound of the formula

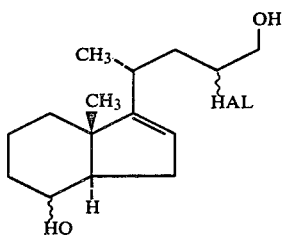

X

Exemplary of suitable reducing agents are diisobutylaluminum hydride and lithium aluminum hydride, with diisobutylaluminum hydride being especially preferred. Exemplary of suitable inert organic solvents are lower aliphatic hydrocarbon solvents such as hexane, heptane, octane and the like, conventional ether solvents such as diethyl ether and tetrahydrofuran, and aromatic hydrocarbons such as benzene and toluene, or lower alkyl halide solvents such as methylene chloride, chloroform, carbon tetrachloride, and the like. The foregoing reaction is carried out a temperatures in the range of about −70° C. to about 80° C., with about 0° C. to about room temperature being preferred.

In the next step, the compound of formula X is reacted with a suitable base in a solvent at temperatures in the range of about −70° C. to about 80° C., with about 0° C. to about room temperature being preferred, so as to yield a compound of the formula

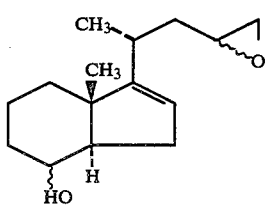

XI

Exemplary of suitable bases are potassium t-butoxide, sodium t-butoxide, potassium isopropoxide, alkali hydroxides such as sodium hydroxide, potassium hydroxide, tri-lower alkylamines, and the like. Exemplary of suitable solvents are lower alkyl alcohols such as methanol, ethanol t-butanol, isopropanol, and the like, and conventional ether solvents such as diethyl ether, and tetrahydrofuran.

In the next step, the compound of formula XI is catalytically hydrogenated by reaction with hydrogen in the presence of a hydrogenation catalyst in an inert organic solvent at temperatures in the range of about 0° C. to about 80° C., with room temperature preferred, so as to yield a compound of the formula

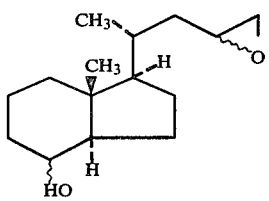

VIa

Exemplary of suitable hydrogenation catalysts are 5% platinum on carbon, 5–10% palladium on carbon, 5–10% rhodium on carbon, platinum oxide and the like. Exemplary of suitable solvents are lower aliphatic hydrocarbon solvents such as hexane, heptane, octane and the like, lower alkyl alcohols such as methanol, ethanol, propanol and the like, conventional ether solvents such as diethyl ether and tetrahydrofuran, and aromatic hydrocarbon solvents such as benzene and toluene, and alkanoic acid alkyl esters such as ethylformate or ethylacetate.

In the next step, if desired, the compound of formula VIa is reacted with an silylating agent under an inert atmosphere at temperatures in the range of from about 0° C. to about 80° C., with room temperature preferred, so as to yield a compound of the formula

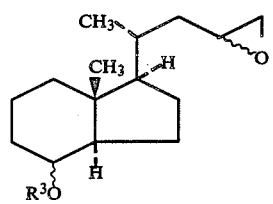

VI wherein $R^3$ is trialkylsilyl, di-loweralkylarylsilyl, lower alkyl diarylsilyl or triarylsilyl. Exemplary of silylating agents are trimethylchlorosilane, triethylchlorosilane, tertiary butyldimethylchlorosilane, chlorodimethylphenylsilane, chlorotriphenylsilane and trimethylsilylimidazole, with trimethylsilylimidazole being especially preferred.

In the alternative, the compound of formula VIa which contains an unprotected hydroxy group may be used as the reagent in the next step.

The compound of formula Ia and its 23,25 diastereomers or mixtures thereof are related to 25-hydroxyvitamin $D_3$ 26,23-lactone, a biologically active vitamin D metabolite reported by Wichmann et al. (Biochemistry, 18, 4775, 1979). The 1α,25-dihydrovitamin $D_3$ 26,23-lactone (same as 1α,23S,25R-trihydroxycholecalciferol-26-oic acid 23,26-lactone) has been disclosed in the prior art as having utility as a therapeutic agent in disorders of calcium and phosphate metabolism. See, for instance, U.S. Pat. No. 4,307,231 and Japanese Pat. No. 57-59881.

The compound of formula Ia and its diastereomers or mixtures thereof can be administered orally, subcutaneously, intramuscularly, intravenously, or intraperitoneally.

The compound of formula I can be formulated into compositions such as tablets, capsules, and the like, or elixirs for oral administration, or in sterile solutions or suspensions for parenteral administration. About 5-20 micrograms of the compound of formula I is compounded with a pharmaceutically acceptable vehicle, carrier, excipient, binder, preservative, stabilizer, flavor, and the like, in a unit dosage as called for by accepted pharmaceutical practice. The amount of active substance in the foregoing compositions or preparations is in the range previously indicated.

Illustrative of the adjuvants which may be incorporated into capsules, and the like are the following: a binder such as gum tragacanth, acacia, corn starch, or gelatin; and excipient such as dicalcium phosphate; a disintegrating agent such as corn starch, potato starch, algenic acid, and the like; a lubricant such as magnesium stearate, a sweetening agent such as sucrose, lactose, or saccharin; a flavoring agent such as peppermint, oil of wintergreen or cherry. Various other materials may be present as coatings or to Sterile compositions for injection can be formulated according to conventional pharmaceutical practice by dissolving or suspending the active substance in a vehicle, such as water for injection, a naturally-occurring vegetable oil, such as sesame oil, coconut oil, peanut oil, cottonseed oil, and the like, or a synthetic fatty vehicle such as ethyl oleate or the like. Buffers, preservatives, antioxidants and the like can be incorporated as required.

The Examples which follow further illustrate the disclosure. All temperatures are in degrees Centigrade unless otherwise stated.

EXAMPLE 1

Preparation of [3R-[3 beta,5S,5 beta(R*),-[1R*(1 beta,3a alpha,4 alpha,7a beta)]]]-dihydro-5-[2-(octahydro-4-trimethylsilyloxy-7a-methyl-1H-inden-1-yl)-2-methylethyl]-3-(1-ethoxyethoxy)-3-methyl-2(3H)-furanone and [3S-[3a alpha,5S,5 beta(R*)-[1R*(1beta,3a alpha,4 alpha,7a beta)]]]dihydro-5-[2-(octahydro-4-trimethyl-silyloxy-7-a-methyl-1H-inden-1-yl)-2-methylethyl]-3-(1-ethoxy-ethoxy)-methyl-2(3H)-furanone.

To a solution of 1.18 g (0.0117 mole) dry diisopropylamine and 20 ml of dry tetrahydrofuran cooled to 0° C. and under an inert atmosphere was added 7.1 ml (0.0107 mole) of n-butyllithium (1.5M in hexane) solution. After 15 minutes, the mixture was cooled to ca. −78° C. and a solution of 1.137 g (0.0080 mole) of 2-(1-ethoxyethoxy)propionitrile in 25 ml of dry tetrahydrofuran was added dropwise. The mixture was stirred 30 minutes then a solution of 0.618 g (0.0020 mole) of [1R-[1 alpha(R*,S*),3a beta,4 beta,7a alpha]]octahydro7a-methyl-1-(1-methyl-2-oxiranyethyl)-1H-inden-4-ol trimethylsilyl ether in 15 ml of dry tetrahydrofuran was added dropwise. The cooling bath was removed and the mixture stirred 2 hours at room temperature, then 7 ml of water was added and the mixture heated to reflux for 20 minutes. 30 ml 1.3M aqueous tartaric acid was added and the mixture was refluxed another 45 minutes. An additional portion of tartaric acid was added to bring the pH to ca 2, the mixture was stirred several minutes then 100 ml of water added and the mixture extracted with 3×50 ml of methylene chloride. The combined extracts were washed with water until neutral then dried over anhydrous sodium sulfate. The mixture was filtered and solvent removed under reduced pressure to give a mixture of [3R-[3 beta,5s,5 beta(R*),[1R* (1beta,3a alpha,4 alpha,7a beta)]]]dihydro-5-[2-(octahydro-4-trimethylsilyloxy-7a-methyl-1H-inden-1-yl)-2-methylethyl]-3-(1-ethoxyethoxy)-3-methyl-2(3H)-furanone and [3S-[3alpha,5S,-beta (R*),[1R*-(1 beta, 3 a alpha,4 alpha,7a beta)]]]dihydro-5-[2-(octahydro-4-trimethylsilyloxy-7a-methyl-1H-inden-1-yl)-2-methylethyl]-3-(1-ethoxyethoxy)-methyl-2(3H)-furanone which was used directly in the next step.

EXAMPLE 2

Preparation of [3R-[3 beta,5S,5 beta(R*)-[1R*-(1 beta, 3a alpha,4 alpha,7a beta)]]]-dihydro-5-[2-(octahydro-4-hydroxy-7a-methyl-1H-inden-1-yl)-2-methylethyl]-3-hydroxy-3-methyl-2(3H)-furanone and [3S-[3 alpha,5S,5 beta(R*),[1R*-(1 beta,3a alpha,4 alpha, 7 a beta)]]]dihydro-5-[2-(octahydro-4-trimethylsilyloxy-7a-methyl-1H inden-1-yl)-2-methylethyl]-3-(1-ethoxyethoxy)-methyl-2(3H)-furanone The crude mixture of [3R-[3 beta,5S,5 beta(R*)-[1R*-(1 beta,3 a alpha,4 alpha, 7a beta)]]]-dihydro-5-[2-(octahydro-4-trimethylsilyloxy-7a-methyl-1H-inden-1-yl)-2methylethyl]-3-(1-ethoxyethoxy)-3-methyl-2(3H)-furanone and [3S-[3 alpha,5S,5 beta(R*)[1R*-(1 beta,3a alpha,4 alpha,7a beta)]]]dihydro-5-[2-(octahydro-4-trimethylsilyloxy-7a-methyl-1H-inden-1-yl)-2-methylethyl]-3-(1-ethoxyethoxy)-3-methyl-2(3H)-furanone obtained from example 1 was dissolved in 100 ml of methanol and stirred with 0.25 g toluenesulfonic acid monohydrate for 35 minutes at room temperature, then solvent was removed under reduced pressure. To the residue was added 150 ml of water and the mixture extracted with 3×50 ml of diethylether-hexane (1:1, v/v%). The combined extracts were washed with brine until neutral then dried over anhydrous sodium sulfate. Filtration and evaporation of solvent under reduced pressure gave 0.635 g of residue. The residue was chromatographed on silica gel eluting with ethyl acetate/hexane/isopropanol (65:32.5:2.5, v/v%) to give 0.247 g (40%) of [3R-[3 beta,5S,(5 beta, (R*)-1R*-(1 beta,3a alpha,4 alpha,7a beta)]]-dihydro-5-[2-(octahydro-4-hydroxy-7a-methyl-1H-inden-1-yl)-2-methylether]-3-hydroxy-3-methyl-2(3H)-furanone, the analytical sample recrystallized from ethyl acetate, mp 129.5°–130.5° C.; $[\alpha]_D^{25} +3.54°$ (c, 0.4545, CHCl$_3$). Calcd. for $C_{18}H_{30}O_4$: C,69.64; H, 9.74. Found: C,69.57; H, 9.94, and 0.189 g of [3S-[3 alpha,5S,5 beta(R*),[1R*-(1 beta,3a alpha,4 alpha,7a beta)]]]dihydro-5-[2-(octahydro-4-hydroxy-7a-methyl-1H-inden-1-yl)-2-methylethyl]-3-hydroxy-3-methyl-2(3H)-furanone, mp 190°–191° C., $[\alpha]_D^{25} -27.59°$ (C, 0.9860, CHCl$_3$).

EXAMPLE 3

Preparation of [3R-[3beta,5S,(5 beta,(R*)-1R*-(1 beta,3a alpha,7a beta)]]dihydro-5-[2-(octahydro-7a-methyl-1H-inden-4-one-1-yl)-2-methylethyl]-3-hydroxy-3-methyl-2(3H)-furanone A solution of 90.0 mg (0.290 mmol) of [3R-[3 beta,5S,(5beta,(R*)-1R*-(1 beta,3a alpha,4alpha,7a beta)]]-dihydro-5-[2-(octahydro-4-hydroxy-7a-methyl-1H-inden-1-yl)-2-methylethyl]-3-hydroxy-3-methyl-2(3H)-furanone in 4 ml. of dry methylene chloride was treated at room temperature with 340.0 mg (1.162 mmol) of 2,2'-bipyridinium chlorochromate for 5.5 hours. A few drops of isopropyl alcohol were then added and the resulting mixture diluted with 50 ml of methylene chloride, filtered through Celite ® filter aid. After evaporation of the solvent, the residue was dissolved in 100 ml. of ethyl acetate, extracted with 3×20 ml. of 1N hydrochloric acid and then with 3×30 ml of brine. The organic phases were combined, dried and evaporated to give 89.0 mg (quantitative yield) of [3R-[3 beta,5S,(5 beta,(R*)-1R*-(1 beta,3a alpha,7a beta)]]-dihydro-5-[2-(octahydro-7a-methyl-1H-inden-4-one-1-yl)-2-methylethyl]-3-hydroxy-3-methyl-2(3H)-furanone.

EXAMPLE 4

Preparation of [3R-[3 beta,5S,(5 beta,(R*)-(1 beta,3a alpha,7a beta)]]-dihydro-5-[2-(octahydro-7a-methyl-1H-inden-4-one-1-yl)-2-methylethyl]-3-trimethylsilyloxy-3-methyl-2(3H)-furanone.

A solution of 89.0 mg (0.289 mmol) of [3R-[3 beta,5S,(5 beta,(R*)-1R*-(1 beta,3a alpha,7a beta)]]-dihydro-5-[2-(octahydro-7a-methyl-1H-inden-4-one-1-yl)-2-methyl-ethyl]-3-hydroxy-3-methyl-2(3H)-furanone in 5 ml of dry tetrahydrofuran was treated with 200 mg (1.426 mmol) of N-trimethylsilylimidazole and the resulting mixture stirred under argon for 4 hours. After this time, 0.5 mL of water was added and, after stirring for an additional 0.2 hours, the resulting mixture was extracted with ethyl acetate. The combined organic phases were washed with brine, dried and evaporated. The residue was purified by fast filtration through a small silica column, eluted with hexane-ethyl acetate (2:1) to give 94.0 mg (86% yield) of [3R-[3 beta,5S,(5 beta,(R*)-1R*-(1 beta,3a alpha, 7a beta)]]-dihydro-5-[2-(octahydro-7-a-methyl-1H-inden-4-one-1-yl)-2-methylethyl]-3-trimethyl-silyloxy-3-methyl-2(3H)-furanone.

EXAMPLE 5

(1 alpha,3 beta,5Z,7E,23S,25R)-1,3-bis[dimethyl-(1,1-dimethylethyl)silyloxy]-23-hydroxy-25-trimethylsilyloxy-9,10-secocholesta-5,7,10(19)-trien-26-oic acid gamma lactone A solution of 260.0 mg (0.446 mmol) of [3S-(3 alpha,5 beta,Z)]-2-[2-methylene-3,5-bis-[(1,1-dimethylethyl)-dimethylsilyloxy]cyclohexyliden]ethyldiphenyl phosphine oxide in 6 ml of dry tetrahydrofuran was cooled at −78° C. and treated dropwise under argon with 0.250 ml (0.425 mmol) of a 1.7 m solution of n-butyllithium in hexane. After stirring for 5 minutes, a solution of 94.0 mg (0.247 mmol) of [3R-[3 beta,5S,(5 beta,(R*)-1R*-(1 beta,3a alpha, 7a beta)]]-dihydro-5-[2-(octahydro-7a-methyl-1H-inden-4-one-1-71)-2-methylethyl]-3-trimethylsiloxy-3-methyl-2(3H)-furanone in 2 mL of dry tetrahydrofuran was slowly added and the resulting mixture stirred at −78° C. for 1.5 hours. It was then treated with 2 mL of a 1:1 mixture of 1N sodium bicarbonate and 1N potassium sodium tartrate, allowed to come to room temperature, diluted with water and extracted with 3×60 mL of ethyl acetate. The combined organic extracts were washed with brine, dried and evaporated. The residue was purified by chromatography on silica, eluting with hexane/ethyl acetate (5:1) to give 160.0 mg of (1 alpha,3 beta,5Z,7E,23S,25R)-1,3-bis[dimethyl-(1,1-dimethylethyl)-silyloxy]-23-hydroxy-25-trimethylsilyloxy-9,10-secocholesta-5,7,10(19)-trien-26-oic acid gamma lactone as a thick colorless oil. This was used directly in the next step (example 6).

EXAMPLE 6

Preparation of (1 alpha,3 beta,5Z,7E,23S,25R)-1,3.23,25-Tetrahydroxy-9,10-secocholesta-5,7,10(19)-trien-26-oic acid gamma Lactone The 160 mg of (1 alpha,3 beta,5Z,7E,23S,25R)-1,3-bis[dimethyl-(1,1-dimethylethyl)silyloxy]-23-hydroxy-25-trimethylsilyloxy-9,10-secocholesta-5,7,10(19)-trien-26-oic acid gamma lactone obtained from example 5 was dissolved in 6 mL of dry methanol, treated with 1.6 g of cation exchange resin (AG 60W-X4, 200–400 mesh, BioRad Laboratories) and stirred overnight. After filtration and washing of the resin with 20 ML of methanol, the solvent was evaporated in vacuo and the residue dissolved in 80 mL of ethyl acetate and washed with 2×20 mL of 2N sodium bicarbonate solution followed by 3×20 mL of brine. The residue obtained after evaporation of the solvent was purified by chromatography on silica, eluting with ethyl acetate to give 101.0 mg (92% yield) of pure (1 alpha,3 beta,5Z,7E,23S,25R)-1,3,23,25-tetrahydroxy-9,10-secocholesta-5,7,10(19)-trien-26 oic acid gamma lactone as white amorphous powder.

EXAMPLE 7

Preparation of [3S-[3 alpha,5S,5 beta (R*),[1R*-(1 beta,3a alpha,7a beta)]]]dihydro-5-[2-(octahydro-7a-methyl-1H-inden-4-one-1-yl)-2-methylethyl]-3-hydroxy-3-methyl-2(3H)-furanone Following the procedure of Example 3, [3S-[3 alpha,5S,5 beta (R*),[1R*-1 beta,3a alpha,4 alpha,7a beta)]]]dihydro-5-[2-(octahydro-4-hydroxy-7a-methyl-1H-inden-1-yl)-2-methylethyl]-3-hydroxy-3-methyl-2(3H)-furanone is converted to [3S-[3 alpha,5S,5 beta (R*),[1R*-(1 beta,3a alpha,7a beta)]]]dihydro-5-[2-(octahydro-7a-methyl-1H-inden-4-one-1-yl)-2-methylethyl]-3-hydroxy-3-methyl-2(3H)-furanone.

EXAMPLE 8

Preparation of [3S-[3 alpha,5R,5 alpha (R*),[1R*-(1 beta,3a alpha,7a beta)]]]dihydro-5-[2-(octahydro-7a-methyl-1H-inden-4-one-1-yl)-2-methylethyl]-3-hydroxy-3-methyl-2(3H)-furanone Following the procedure of Example 3, [3S-[3 alpha,5R,5 alpha (R*),[1R*-(1 beta,3a alpha,4 alpha,7a beta)]]]dihydro-5-[2-(octahydro-4-hydroxy-7a-methyl-1H-inden-1-yl)-2-methylethyl]-3-hydroxy-3-methyl-2(3H)-furanone was converted to [3S-[3 alpha,5R,5 alpha (R*),[1R*-(1 beta,3a alpha,7a beta)]]]dihydro-5-[2-(octahydro-7a-methyl-1H-inden-4-one-1-yl)-2-methylethyl]-3-hydroxy-3-methyl-2(3H)-furanone.

EXAMPLE 9

Preparation of [3R-[3 beta,5R,5 alpha(R*),[1R*-(1 beta,3a alpha,7a beta)]]]dihydro-5-[2-(octahydro-7a-methyl-1H-inden-4-one-1-yl)-2-methylethyl]-3-hydroxy-3-methyl-2(3H)-furanone Following the procedure of Example 3, [3R-[3 beta,5R, 5 alpha(R*),[1R*-(1 beta,3a alpha,4 alpha,7a beta)]]]dihydro-5-[2-(octahydro-4-hydroxy-7a-methyl-1H-inden-1-yl)-2-methylethyl]-3-hydroxy-3-methyl-2(3H)-furanone is converted to [3R-[3 beta,5R,5 alpha(R*),[1R*-(1 beta,3a alpha,7a beta)]]]dihydro-5-[2-(octahydro-7a-methyl-1H-inden-4-one-1-yl)-2-methylethyl]-3-hydroxy-3-methyl-2(3H)-furanone.

EXAMPLE 10

Preparation of [3S-[3 alpha,5S,5 beta(R*)[1R*-(1 beta,3a alpha,7a beta)]]]dihydro-5-[2-(octahydro-7a-methyl-1H-inden-4-one-1-yl)-2-methylethyl]-3-trimethylsilyloxy-3-methyl-2(3H)-furanone Following the procedure of Example 4, [3S-[3 alpha,5S,5 beta(R*)[1R*-(1 beta,3a alpha,7a beta)]]]dihydro-5-[2-(octahydro-7a-methyl-1H-inden-4-one-1-yl)-2-methyl-ethyl]-3-hydroxy-3-methyl-2(3H)-furanone is converted to [3S-[3 alpha,5S,5 beta(R*)[1R*-(1 beta,3a alpha,7a beta)]]]dihydro-5-[2-(octahydro-7a-methyl-1H-inden-4-one-1-yl)-2-methylethyl]-3-trimethyl-silyloxy-3-methyl-2(3H)-furanone.

EXAMPLE 11

Preparation of [3S-[3 alpha,5R,5 alpha(R*)[1R*-(1 beta, 3a alpha,7a beta)]]]dihydro-5-[2-(octahydro-7a-methyl-1H-inden-4-one-1-yl)-2-methylethyl]-3-trimethylsilyloxy-3-methyl-2(3H)-furanone Following the procedure of Example 4, [3S-[3 alpha,5R,5 alpha(R*)[1R*-(1 beta,3a alpha,7a beta)]]]dihydro-5-[2-(octahydro-7a methyl-1H-inden-4-one-1-yl)-2-methyl-ethyl]-3-hydroxy-3-methyl-2(3H)-furanone was converted to [3S-[3 alpha,5R,5 alpha(R*)[1R*-(1 beta, 3a alpha,7a beta)]]]dihydro-5-[2-(octahydro-7a-methyl-1H-inden-4-one-1-yl)-2-methylethyl]-3-trimethyl-silyloxy-3-methyl-2(3H)-furanone.

EXAMPLE 12

Preparation of [3R-[3 beta,5R,5 alpha(R*)[1R*-(1 beta,3a alpha,7a beta)]]]dihydro-5-[2-(octahydro-7a-methyl-1H-inden-4-one-1-yl)-2-methylethyl]-3-trimethylsilyloxy-3-methyl-2(3H)-furanone Following the procedure of Example 4, [3R-[3 beta,5R,5 alpha(R*)[1R*-(1 beta,3a alpha,7a beta)]]]dihydro-5-[2-(octahydro-7a-methyl-1H-inden-4-one-1-yl)-2-methyl-ethyl]-3-hydroxy-3-methyl-2(3H)-furanone is converted to [3R-[3 beta,5R,5 alpha(R*)[1R*-(1 beta, 3a alpha,7a beta)]]]dihydro-5-[2-(octahydro-7a-methyl-1H-inden-4-one-1-yl)-2-methylethyl]-3-trimethyl-silyloxy-3-methyl-2(3H)-furanone.

EXAMPLE 13

Preparation of (1 alpha,3 beta,5Z,7E,23R,25S)-1,3-bis[dimethyl-(1,1-dimethylethyl)silyloxy]-23-hydroxy-25-trimethylsilyloxy-9,10-secocholesta-5,7,10(19)-trien-26-oic acid gamma lactone Following the procedure of Example 5, [3S-[3 alpha,5R,5 alpha(R*)[1R*-(1 beta,3a alpha,7a beta)]]]dihydro-5-[2-(octahydro-7a-methyl-1H-inden-4-one-1-yl)-2-methylethyl]-3-trimethylsiloxy-3-methyl-2(3H)-furanone was converted to (1 alpha,3 beta,5Z,7E,23R,25S)-1,3-bis(dimethyl-(1, 1-dimethylethyl)-silyloxy]-23-hydroxy-25-trimethylsilyloxy-9,10-secocholesta-5,7,10(19)-trien-26-oic acid gamma lactone.

EXAMPLE 14

Preparation of (1 alpha, 3 beta,5Z,7E,23R,25R)-1,3-bis[-dimethyl-(1,1-dimethylethyl)silyloxy]-23-hydroxy-25-trimethylsilyloxy-9,10-secocholesta-5,7,10(19)-trien-26-oic acid gamma lactone Following the procedure of Example 5, [3R-[3 beta,5R,5 alpha(R*),[1R*-(1 beta,3a alpha,7a beta)]]]-dihydro-5-[2-(octahydro-7a-methyl-1H-inden-4-one-1-yl)-2-methylethyl]-3-trimethylsiloxy-3-methyl-2(3H)-furanone is converted to (1 alpha,3 beta,5Z,7E,23R,25R)-1,3-bis[dimethyl-(1,1-dimethylethyl)-silyloxy]-23-hydroxy-25-trimethylsilyloxy-9,10-secocholesta-5,7,10(19)-trien-26-oic acid gamma lactone.

EXAMPLE 15

Preparation of (1 alpha,3 beta,5Z,7E,23S, 25S)-1,3-bis[-dimethyl-(1,1-dimethylethyl)silyloxy]-23-23-hydroxy-25-trimethylsilyloxy-9,10-secocholesta-5,7,10(19)-trien-26-oic acid gamma lactone Following the procedure of Example 5, [3S-[3 alpha,5S,5 beta(R*),[1R*-(1 beta,3a alpha,7a beta)]]]-dihydro-5-[2-(octahydro-7a-methyl-1H-inden-4-one-1-yl)-2-methylethyl]-3-trimethylsiloxy-3-methyl-2(3H)-furanone is converted to (1 alpha,3 beta,5Z,7E,23S,25S)-1,3-bis[dimethyl-(1,1-dimethylethyl)-silyloxy]-23-hydroxy-25-trimethylsilyloxy-9,10-secocholesta-5,7,10(19)-trien-26-oic acid gamma lactone.

EXAMPLE 16

Preparation of (1 alpha,3 beta,5Z,7E,23R,25R)-1,3,23,25-tetrahydroxy-9,10-secocholesta-5,7,10(19)-trien-26-oic acid gamma lactone Following the procedure of Example 6, (1 alpha,3 beta,5Z,7E,23R,25R)-1,3-bis[dimethyl-(1,1-dimethylethyl)silyloxy]-23-hydroxy-25-trimethylsilyloxy-9,10-secocholesta-5,7,10(19)-trien-26-oic acid gamma lactone is converted to (1 alpha,3 beta,5Z,7E,23R,25R)-1,3,23,15-tetrahydroxy-9,10-secocholesta-5,7,10(19)-trien-26 oic acid gamma lactone.

EXAMPLE 17

Preparation of (1 alpha,3 beta,5Z,7E,23R,25S)-1,3,23,25-tetrahydroxy-9,10-secocholesta-5,7,10(19)-trien-26-oic acid gamma lactone Following the procedure of Example 6, (1 alpha,3 beta,5Z,7E,23R,25S)-1,3-bis[dimethyl-(1,1-dimethylethyl)silyloxy]-23-hydroxy-25-trimethylsilyloxy-9,10-secocholesta-5,7,10(19)-trien-26-oic acid gamma lactone was converted to (1 alpha,3 beta,5Z,7E,23R,25S)-1,3,23,25-tetrahydroxy-9,10-secocholesta-5,7,10(19)-trien-26 oic acid gamma lactone.

EXAMPLE 18

Preparation of (1 alpha,3 beta,5Z,7E,23S, 25S)-1,3,23,25-tetrahydroxy-9,10-secocholesta-5,7,10(19)-trien-26-oic acid gamma lactone Following the procedure of Example 6, (1 alpha,3 beta,5Z,7E,23S,25S)-1,3-bis[dimethyl-(1,1-dimethylethyl)silyloxy]-23-hydroxy-25-trimethylsilyloxy-9,10-secocholesta-5,7,10(19)-trien-26-oic acid gamma lactone is converted to (1 alpha,3 beta,5Z,7E,23S,25S)-1,3,23,25-tetrahydroxy-9,10-secocholesta-5,7,10(19)-trien-26 oic acid gamma lactone.

EXAMPLE 19

Preparation of [3R-[3 beta,5R,5 alpha(R*),[1R*(1 beta,3 alpha,4 alpha,7a beta)]]]dihydro-5-[2-(octahydro-4-trimethylsilyloxy-7a-methyl-1H-inden-1-yl)-2-methylethyl]-3-(1-ethoxyethoxy)-3-methyl-2(3H)-furanone and [3S-[3 alpha,5R,5 alpha(R*),[1R*(1 beta,3a alpha,4 alpha,7a beta)]]]dihydro-5-[2-(octahydro-4-trimethylsilyloxy-7a-methyl-1H-inden-1-yl)-2-methylethyl]-3-(1-ethoxyethoxy)-methyl-2(3H)-furanone Following the procedure of example 1, [1R-[1 alpha(R*, R*),3a beta,4 beta,7a alpha]]octahydro-7-methyl-1-(1-methyl-2-oxiranyethyl)-1H-inden-4-ol trimethylsilyl ether was converted to [3R-[3 beta,5R,5 alpha,(R*),[1R*(1 beta,3 alpha,4 alpha,7a beta]]]dihydro-5-[2-(octahydro-4-trimethylsilyloxy-7a-methyl-1H-inden-1-yl)-2-methylethyl]-3-(1-ethoxyethoxy)-3-methyl-2(3H)-furanone and [3S-[3 alpha,5R,5-alpha,(R*),[1R*-(1 beta,3a alpha,4 alpha,7a beta)]]]dihydro-5-[2-(octahydro-4-trimethylsilyloxy-7a-methyl-1H inden-1-yl)-2-methylethyl]-3-(1-ethoxyethoxy)-methyl-2(3H)-furanone which were used directly in example 20.

EXAMPLE 20

Preparation of [3R-[3 beta,5R,5 alpha,(R*),[1R*(1 beta,3 alpha,4 alpha,7a beta)]]]dihydro-5-[2-(octahydro-4-hydroxy-7a-methyl-1H-inden-1-yl)-2-methylethyl]-3-hydroxy-3-methyl-2(3H)-furanone and [3S-[3 alpha,5R,5 alpha,(R*),-[1R*(1 beta,3 alpha,4 alpha,7a beta)]]]dihydro-5-[2-(octahydro-4-hydroxy-7a-methyl-1H-inden-1-yl)-2-methylethyl]-3-hydroxy-3-methyl-2(3H)-furanone Following the procedure of example 2, [3R-[3 beta,5R,5 alpha,(R*),[1R*(1 beta,3 alpha,4 alpha,7a beta)]]]dihydro-5-[2-(octahydro-4-trimethylsilyloxy-7a-methyl-1H-inden-1-yl)-2-methylethyl]-3-(1-ethoxyethoxy)-3-methyl-2(3H)-furanone and [3S-[3 alpha,5R,5 alpha(R*),[1R*-(1 beta,3a alpha,7a beta)]]]dihydro-5-[2-(octahydro-4-trimethylsilyloxy-7a-methyl-1H inden-1-yl)-2-methylethyl]-3-(1-ethoxyethoxy)-methyl-2(3H)-furanone were converted to [3R-[3 beta,5R,5 alpha,(R*)-[1R*(1 beta,3 alpha,4 alpha,7a beta)]]]dihydro-5-[2-(octahydro-4-hydroxy-7a-methyl-1H-inden-1-yl)-2-methylethyl]-3-hydroxy-3-methyl-2(3H)-furanone mp 166°-167° C., $[\alpha]_D^{25} = +58.39°$ (C, 0.3819, CHCl$_3$) and [3S-[3 alpha,5R,5 alpha(R*),-[1R*(1 beta,3 alpha,4 alpha,7a beta)]]]dihydro-5-[2-(octahydro-4-hydroxy-7a-methyl-1H-inden-1-yl)-2-methylethyl]-3-hydroxy-3-methyl-2(3H)-furanone, mp 151°-152° C., $[\alpha]_D^{25} = +33,47°$ (C, 0.9800, CHCl$_3$) respectively.

We claim:

1. A process for the preparation of 1α,23,25-trihydroxycholecalciferol-26-oic acid 23,26-lactone of the formula

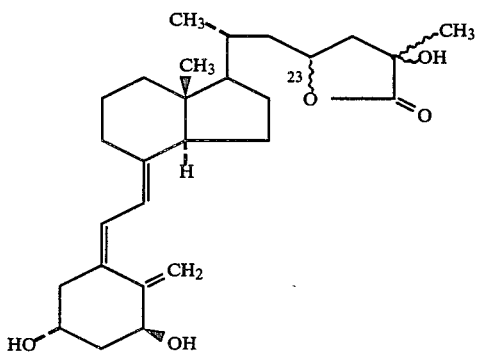

which comprises the steps of
(a) reacting a compound of the formula

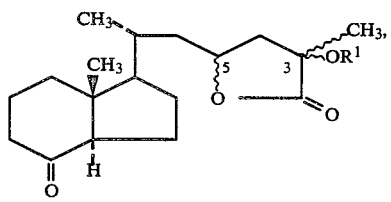

wherein R$^1$ is hydrogen, tri-lower alkylsilyl, aryl-di-lower alkylsilyl, diaryl-lower alkylsilyl or tria-rylsilyl, with a compound of the formula

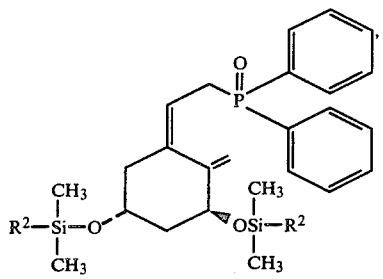

wherein R$^2$ is lower alkyl or aryl, to yield a compound of the formula

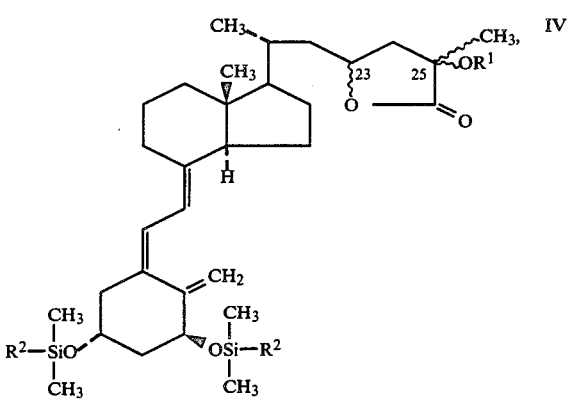

wherein R$^1$ and R$^2$ are previously described, and
(b) removing the protecting groups from whereby there is obtained the corresponding compound of formula I.

2. A process in accordance with claim 1, wherein R$^1$ is lower alkyl and R$^2$ is tri-lower alkylsilyl or hydrogen.

3. A process in accordance with claim 2, wherein the removal of the protecting groups is effected by treating the compound of formula IV with a lower alkyl alcohol in the presence of a cationic ion exchange resin.

4. A process, in accordance with claim 1, for the preparation of 1α,23S,25R-trihydroxy-cholecalciferol-26-oic acid gamma lactone of the formula

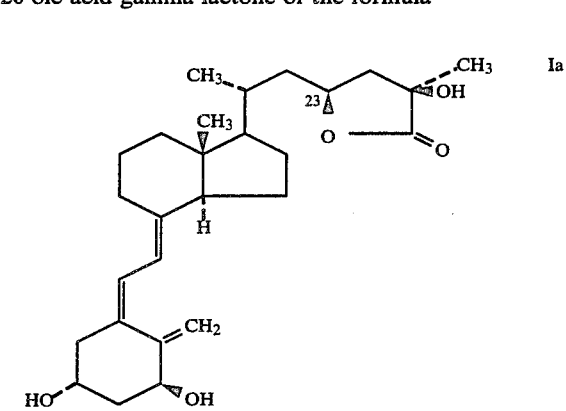

which comprises the steps of
(a) reacting a compound of the formula

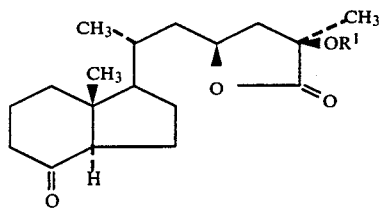

wherein R¹ is hydrogen, tri-lower alkylsilyl, aryl-di-lower alkylsilyl, lower alkyldi-arylsilyl, or triarylsilyl with a compound of the formula

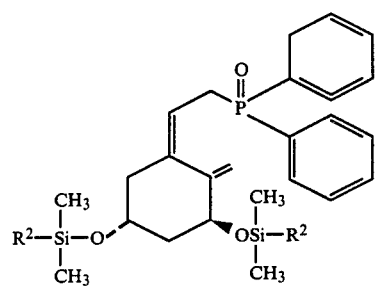

wherein R² is lower alkyl or aryl to yield a compound of the formula

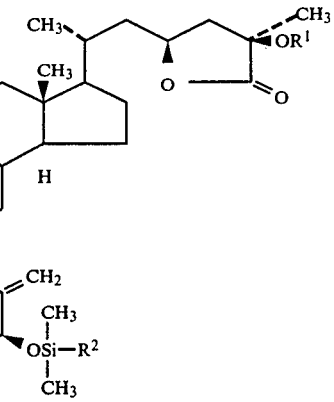

wherein R¹ and R² are as above, and (b) removing the protecting groups from a compound of formula IV whereby there is obtained the compound of formula I.

5. A process in accordance with claim 4, wherein R¹ is tri-lower alkylsilyl or hydrogen and R² is lower alkyl.

6. A process in accordance with claim 5, wherein the removal of the protecting groups is effected by treating the compound of formula IVa with a lower alkyl alcohol in the presence of a cationic ion exchange resin.

* * * * *